United States Patent [19]

Frank et al.

[11] Patent Number: 5,830,903
[45] Date of Patent: Nov. 3, 1998

[54] TRIAZOLE SUBSTITUTED QUINOLINE DERIVATIVES FOR GASTROINTESTINAL TREAT-TREATMENT

[75] Inventors: Laszlo Frank, Tiszavasvari; Klara Gyires; Andras Bilkei-Gorzo, both of Budapest; Ferenc Korodi; Vilmos Galamb, both of Tiszavasvari, all of Hungary

[73] Assignee: Alkaloida Chemical Co., Ltd., Tiszavasvari, Hungary

[21] Appl. No.: 343,576

[22] PCT Filed: Mar. 31, 1994

[86] PCT No.: PCT/HU94/00008

§ 371 Date: Jan. 29, 1996

§ 102(e) Date: Jan. 29, 1996

[87] PCT Pub. No.: WO94/22413

PCT Pub. Date: Oct. 13, 1994

[30] Foreign Application Priority Data

Apr. 1, 1993 [HU] Hungary .................... P 93 00948

[51] Int. Cl.⁶ .................... A61K 31/47; C07D 401/04
[52] U.S. Cl. .................... 514/314; 546/153
[58] Field of Search ............ 546/153; 514/260, 514/312, 314; 544/331

[56] References Cited

U.S. PATENT DOCUMENTS 4,772,613  9/1988  Parsons et al. .................... 514/309
5,104,884  4/1992  Korodi et al. .................... 514/312

FOREIGN PATENT DOCUMENTS

0221947B1  11/1990  European Pat. Off. ...... C07D 401/04

*Primary Examiner*—C. Warren Ivy
*Assistant Examiner*—Charanjit S. Aulakh
*Attorney, Agent, or Firm*—Steinberg, Raskin & Davidson, P.C.

[57] ABSTRACT

The invention relates to pharmaceutical compositions for the treatment or prevention of lesions of gastrointestinal mucous membranes and having secretion inhibiting, cytoprotective activities. The compositions contain in a biologically effective quantity a triazole-group-substituted quinoline derivative of general formula (I)

$R^1$ stands for a 1-triazolyl-group in position 2 or 4 or
   a 3-triazolyl-thio or
   a 5-/$C_{1-4}$-alkyl/-3-triazolyl-thio-group, $R^2$ stands for a hydrogen atom in position 3 or optionally in position 2, or for a $C_{1-4}$-alkyl-group, $R^3$ stands for a hydrogen atom or for a $C_{1-4}$-alkyl-group, X stands for a hydrogen or halogen-atom or for a $C_{1-4}$-alkyl-group or its salts. The invention includes processes for the preparation of the above compositions, and methods for treatment of patients in need of such treatment by administering the substance or the composition. The prefered substance of formula (IV) is also subject of the invention.

19 Claims, 1 Drawing Sheet

TRIAZOLE SUBSTITUTED QUINOLINE DERIVATIVES FOR GASTROINTESTINAL TREAT-TREATMENT

This application is 371 of PCT/HW94/00008 which is now published as WO94/22413.

The invention is related to pharmaceutical compositions for protection and treatment of lesions of gastrointestinal mucous membrans and having secretion inhibiting and cytoprotective activity. More particularly the invention is related to pharmaceutical compositions containing as active ingredient certain quinoline derivatives and their salts in a biologically effective quantity optionally together with other active pharmaceutical ingredients, processes for their preparation and methods of treatment to use them alone or in combination with other pharmaceutically active ingredients.

In this specification the substituents of varying interpretation stand always for the following:

$R^1$ stands for a 1-triazolyl-group in position 2 or 4, or
  a 3-triazolyl-thio-group or
  a 5-/$C_{1-4}$-alkyl/-3-triazolyl-thio-group, $R^2$ stands for a hydrogen atom in position 3 or optionally in position 2 or for a C1-4-alkyl-group, $R^3$ stands for a hydrogen atom or a $C_{1-4}$-alkyl-group, X stands for a hydrogen or halogen-atom or for a $C_{1-4}$-alkyl group.

It is accepted knowledge that peptic ulcer of the upper digestive tract is caused as a result of a disequilibrium between the defensive factors (force of mucosal resistance) and agressive factors (gastric acid and pepsin secretion) /e.g. Nature 236, 358,1972/. Pharmaceuticals inhibiting secretion are well known. Part of them are anticholinergs and histamine $H_2$-receptor antagonists such as e.g. cimetidin, ranitidine, famotidin, others are potassium ATP-ase inhibitors such as omeprasole. These drugs are effective against gastric and intestinal ulcer however on terminating their administration the ulcers reappear in a high ratio of patients especially in cases where the patients do not receive antiacidic drugs (Med.Res.Rev.10., 1, 1990).

Another possibility to fight against ulcer resides in the intensification of the protective factors. Protective mechanism is accomplished through the mucosal barrier which protects the gastric mucous membrane from the noxious effects of the luminal pepsin and hydrogen ions. The protection stands under a multifactoral control:

a mucous protective layer covering the gastric mucous membrane which ensures a non-mixing layer on the surface,
  bicarbonate secretion, causing a pH-change between the lumen of the stomach (pH=2,0) and the center of the mucous membrane cells (pH=7),
  regeneration of the mucous membrane and
  blood supply from the submucosa.

All four of the above are influenced by the synthesis of the so called cytoprotective prostaglandins. (Contemporary issues in Gastroenterology Vol 3, Chapters 5 to 8, New York, 1985, Ed: Cohen and Saloway).

The non-steroidal antiinflammatory drugs (NSAID) like aspirin, indomethacin, naproxen, piroxicam etc. act by inhibiting the activity of the cyclooxygenase enzyme controlling the synthesis of prostaglandins to a different extent. However it has been shown that as a consequence of inhibiting activity of the cyclooxygenase during treatment with NSAIDs, the local prostaglandin $E_2$ concentration of the gastric mucous membran is decreased resulting in erosions and ulcers (e.g. Lancet,2, 1253–54, 1978).

There are but some prostaglandin derivatives known (e.g. misoprostol) which were able to stop the damage of the gastric mucous membrane when administered after NSAID treatment (Scand. J. Gastroenterol. 9.page 751, 1974; 94, page 1973, 1988). Most of the known gastroprotectives however have to be administered before NSAID treatment.

Thus there is a need for an effective biological agent which is able on the one side to decrease gastric acidity and on the other hand to intensify the protective factors of the mucosa. This might result in a drug which might be administered together or after NSAID treatment for effective prevention or therapy of gastroenteropathy induced by NSAIDs.

SUMMARY OF THE INVENTION

One object of the present invention are pharmaceutical compositions for the treatment or prevention of lesions of gastrointestinal mucous membranes having secretion inhibiting and cytoprotective activities containing in a biologically effective quantity a triazole-group-substituted quinoline derivative of general formula (I) or its salts.

According to a previous patented invention a greater group of certain quinoline-derivatives containing a triazole groups was disclosed including also those of general formula (I). Their use as analgesics and antiphlogistics was shown on various pharmacological tests along with their fungistatic activity against phytopathogenic fungal pests (EP 0221947 or corresponding U.S. Pat. No. 5,104,884).

When further investigating said agents we have found that some of the substances, namely the compounds of general formula (I) exhibit a considerable gastroprotective activity. It was highly unexpected to find a smaller group of substances showing gastroprotective activity in a group of antiinflammatories acting supposedly on cyclooxygenase inhibiting basis (the NSAIDs known hitherto were all considered cyclooxygenase inhibitors). This suggests that the gastroprotecting activity found has a different mechanism of activity as compared with those known to date. We have investigated the substances against several types of experimental ulcers showing different pathomechanisms. The details of the investigations and results are shown in Biological Examples I.1. to I.8. The results can be summarized as follows:

1. The compounds inhibit to a high degree, significantly, in a dose-dependent manner the injuries of the mucosa caused by NSAIDs such as indomethacin, naproxen, piroxicam (Tables I and II)
2. The substances reduce secretion of the gastric acid as shown on Shay rats both on basic gastric acid secretion and on secretion stimulated with histamine (Tables III and IV). Both quantity of the gastric acid and acidity are decreased as a consequence of treatment.
3. The substances have cytoprotective activity. When severe necrosis, deep ulcer was caused on glandular parts of the gastric region by treatment with hydrochloric acid in ethanol regions were brought into equilibrium by the substances according to the invention as shown in Table V in comparison with cimetidine. The latter was used in standard doses of 100 mg/kg and found practically ineffective in this test.
  The substances inhibit increase of permeability of the injured blood-vessels in a significant manner when administered in 10 and 20 mg/kg doses as shown on substance 1 in Table VI. This mechanism may play an important role in the anti-ulcer activity of our substances.
4. Significant inhibition of gastric mucous membrane lesions caused by stress situations was found in 10-25-50 mg/kg oral doses as shown in Table VII.

5. It was found further that some of the substances cause a significant increase of the gastric blood supply in the region of the corpus and the atrum. This could be shown using the method of Sapistain with $Rb^{86}$ isotope investigations as stated in Table VIII.

Summarizing the above it is clear that the substances according to the invention show strong and lasting activity on ulcer models having different activity mechanisms. Their spectrum of activity is broad. They develop their protective activity both in a profilactic manner and when given after certain inductive agents and they promote natural healing of ulcers and erosions.

On the basis of the above finding we suppose that our substances show a unique mechanism of activity and that the substances do not fit easily into any known group of ulcer-inhibiting drugs. Eg: Their inhibiting activity on hyperacidity is independent from the blocade of the cholinerg and the H2-receptors. Their activity against ethanol+hydrochloric acid gives led to our supposition that cytoprotective activity has to be present. The increased mucosal blood microcirculation has to be one of the factors resulting in this cytoprotective activity along with other unknown further correlations etc.

The products according to the invention thus might be used in prevention and treatment of lesions of the gastrointestinal mucous membranes, ulcers, erosions based on different pathomechanisms. They act favourably on both active and defensive ulcer-influencing factors. They are a possibility of a new way in ulcer therapy.

Preferred pharmaceutical compositions according to the invention are those containing a quinoline derivative of general formula (II) or its salts in a biologically effective quantity.

Another advantageous group of the above compositions according to the invention are compositions containing a quinoline derivative of general formula (III) or its salts in a biologically effective quantity.

Some of the substances which can be used as such or as salts in a biologically effective quantity in compositions according to the invention are the following:

4-(1H-1,2,4-triazole-1-yl)-quinoline,
4-(1H-1,2,4-triazole-1-yl)-7-halogen-quinolines,
4-(1H-1,2,4-triazole-1-yl)-7-chloro-quinoline,
4-(1H-1,2,4-triazole-1-yl)-7-($C_{1-4}$alkyl)-quinolines,
2-methyl-4-(1H-1,2,4-triazole-1-yl)-quinoline,
2-(1H-1,2,4-triazole-1-yl)-quinoline,
2-(1H-1,2,4-triazole-1-yl)-3-($C_{1-4}$alkyl)-quinolines,
2-(1H-1,2,4-triazole-1-yl)-3-methyl-quinoline,
2-(1H-1,2,4-triazole-1-yl)-3-($C_{1-4}$alkyl)-7-halogen-quinolines,
2-(1H-1,2,4-triazole-1-yl)-3-methyl-7-bromo-quinoline,
2-(1H-1,2,4-triazole-1-yl)-3-methyl-7-chloro-quinoline,
2-(1H-1,2,4-triazole-1-yl)-3-($C_{1-4}$alkyl)-7-($C_{1-4}$alkyl)-quinoline,
2-(1H-1,2,4-triazole-1-yl)-3-methyl-7-ethyl-quinoline,
2-($C_{1-4}$alkyl)-4-(1H-1,2,4-triazole-1-yl-thio)quinoline,
2,5,7-trimethyl-4-(5-ethyl-1H-1,2,4-triazole-3-yl-thio)-quinoline,
2-(1H-1,2,4-triazole-3-yl-thio)-3-($C_{1-4}$alkyl)-quinolines,
2-(5-ethyl-1H-1,2,4-triazole-3-yl-thio)-3-methyl-quinoline,
2-(1H-1,2,4-triazole-3-yl-thio)-3-methyl-quinoline.

One or more substances of Formula (I) can be incorporated into the compositions. The salts may be formed with any pharmaceutically acceptable acid. Acids of preference are e.g. hydrochloric acid, sulfuric acid, ortho-phosphoric acid, oxalic acid, citric acid, maleic acid, tartaric acid and the like.

A further embodiment of the present invention are pharmaceutical compositions for the treatment or prevention of lesions of gastric mucous membranes and having secretion inhibiting, cytoprotective activities containing a quinoline derivative of general formula (I) or its salts in a biologicaly effective quantity together with inert, pharmaceutically acceptable accompanying products or in admixture with the same.

Another further feature of the invention are processes for the preparation of the above pharmaceutical compositions of secretion inhibiting, cytoprotective activity, especially for the treatment or prevention of ulcer by way of formulating the active ingredient of general formula (I) by admixture with accompanying and/or additive products usually used in pharmaceutical production.

The compositions may appear in any known pharmaceutically acceptable form for direct administration perorally, rectally, or by injections or other ways.

A further embodiment of the present invention is a method for treatment or prevention of lesions of the gastrointestinal mucous membranes with inhibition of secretion and with cytoprotection by administering to the patient in need of such treatment a quinoline derivative of general formula (I) or its salts preferably orally or rectally in a daily dose of 5 to 30 mg active ingredient per kg body weight.

The composition according to the invention may contain at least one of the compounds of general formula (I) or its salts with no further biologically active ingredient. However according to a further embodiment of the present invention compositions are provided containing further biologically active ingredients preferably active ingredients having antiinflammatory activity. The substances according to the invention may be administered before or after or parallel with administration of the antiinflammatory agent.

The compounds according to our invention can be prepared according to known methods /EP 0221947 or U.S. Pat. No. 5,104,884/. However in the following chemical examples are given for the preparation of the most important substances. The compound of formula (IV) is one preferred substance which can be used according to the present invention. Since this compound was not disclosed in the above patent specifications preparation and characteristics of this chemical substance are given in detail and protection of this substance and its salts is one further aspect of the present invention.

The compositions according to the invention can be used orally, parenterally in intramuscular or intravenous injectables or rectally. A transdermal application is also possible using known transdermal means, compositions and/or additives.

The dose of administration highly depends from the patient, severity of the case and the mode of administration. For oral treatment daily doses starting from 1.0 mg/kg body weight to 200 mg/kg body weight can be used. It is preferable to use a daily dose of 5 to 30 mg active ingredient per kg body weight.

One dosage unit may contain 10–250 mg preferably 30 to 150 mg of the active ingredient/s/ for oral use. For parenteral use one dose unit contains 1 to 75 mg of the active ingredient, preferably 5–30 mg per unit.

The content of the active ingredient in the compositions according to the invention may vary from about 0,01 to about 99.99% and accordingly the auxiliary products in the compositions may amount to about 99.99 to 0.01%.

In order to prepare the compositions according to the invention liquid or solid additive material can be used. The products may be in form of tablets, dragees, pills, capsules, powders, solutions, suspensions, elixirs. They may be formulated as controlled release tablets.

Carriers used in the compositions according to the invention may be different oils, preferably of animal or plant origin or synthetic oils. Preferred are hazel-nut oil, soy oil, sesame oil etc. Further liquid carriers especially for injectables are water, a physiological salt solution, an aqueous dextrose solution, glycol etc.

Further pharmaceutically acceptable carriers and auxiliary products are starch, cellulose, talc, glucose, lactose, saccharose, gelatin, malt, rice, silica gel, magnesium stearate, milk powder, glycerol, propylene glycol, ethanol etc.

Preferred methods for the treatment of patients is the oral, the parenteral or the rectal form. It might be useful to administer the pharmaceutical compositions several times a day or in a controlled release formulation.

Veterinary compositions and use are included into the scope of the invention.

DETAILED DESCRIPTION OF THE INVENTION

Figure 1:
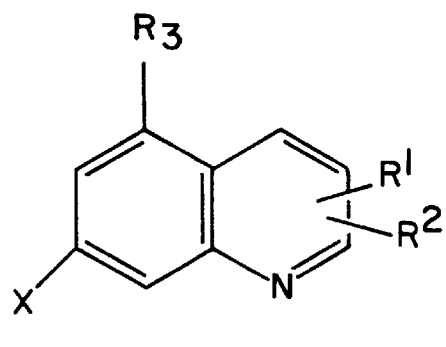
FIGS. 1–4 represent formulae for quinoline derivatives in accordance with the present invention.
Figure 2:
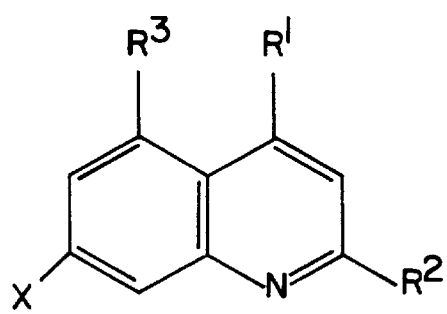
Figure 3:
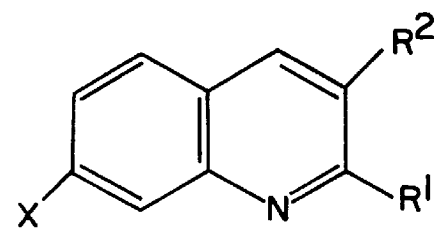
Figure 4:
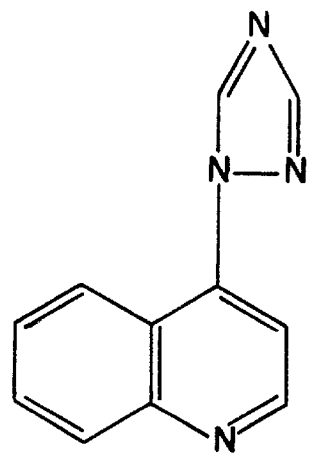

Further aspects of the invention are demonstrated in the Examples without the intention of any limitation to the contents of the same.

EXAMPLES

I. Biological Examples

Example I.1.

Female OFA-rats of 140–180 g weight were starved for 24 hours then treated orally first with different doses of the compounds to be investigated and after 60 minutes with 20 mg/kg of indomethacin. The compounds were administered in a volume of 0.5 ml/100 g in a suspension prepared in water with 2–4% Tween-80. After 6 hours the animals were over-anesthesized and their stomachs were opened along the greater curvature. The preparations were investigated by stereomicroscopy using an 8-fold enlargement. The number, size and incidence of erosions and ulcers was noted and compared with the control group treated with the carrier only.

The size of the ulcers was determined on the basis of the following score:

1: ulcer or erosion of the size of 1–2 mm;
2: ulcer or erosion of the size of 2–3 mm;
3: ulcer or erosion of the size of 3–4 mm;
4: ulcer longer than 4 mm;
5: ulcer longer and broader than 4 mm.

The $ED_{50}$ values were calculated on the basis of ulcer-indexes:

ulcer index=/severeity of lesion x number of lesions/ number of animals /n/

The results are shown in Table I.

TABLE I

| Substance N° | $ED_{50}$ mg/kg (p.o.) /confidence limits 95%/ | Substance N° | $ED_{50}$ mg/kg (p.o.) /confidence limits 95%/ |
|---|---|---|---|
| 1 | 13 /7.2–15.3/ | 8 | 40 /22.8–60.2/ |
| 2 | 53 /41.7–63.8 | 11 | 14 /9.8–19.9/ |
| 3 | 74 /59.6–88.4/ | 12 | 74 /54.0–86.3/ |
| 4 | 44 /32.9–54.5/ | 9 | 47 /32.7–62.8/ |
| 5 | 38 /2.4–56.8/ | 10 | 74 /58.6–89.2/ |
| 6 | 29 /17.0–35.5/ | cimetidine | 96 /78–112/ |
| 7 | 34 /21.6–48.4/ | | |

The above show that lesions caused by intomethacin are strongly decreased by the test samples. In some cases the effect is 2–6 times stronger than the effect caused by cimetidin.

Example I.2.

60 mg/kg piroxicam or 75 mg/kg naproxen were injected orally to WISTAR rats of 150–170 g weight after 24 hours of starvation. Administration of the test substances followed 1 hour after injection. After 4 hours the animals were over-anesthesized with ether and the changes (erosions) were evaluated as in Example I.1. The size of the lesions was characterized by way of the ulcer index. The results are shown in Table II.

TABLE II

| substance No | n | dose mg/kg po. | ulcus index ± SEM | inhibition % |
|---|---|---|---|---|
| naproxen | 7 | 75 | 25.2 ± 6.1 | — |
| naproxen + 1 | 7 | 75 + 20 | 15.6 ± 6.4 | 39 |
| | 7 | 30 | 1.2 ± 0.5** | 95 |
| piroxicam | 7 | 60 | 23.3 ± 6.4 | |
| piroxicam + 1 | 7 | 60 + 20 | 3.8 ± 0.4* | 84 |
| | 7 | 30 | 1.8 ± 0.5** | 93 |

**$p < 0.01$
*$p < 0.05$
p = significance

Table II. shows that the test samples reduce lesions caused by the NSAIDs naproxen and prixocam which are prostaglandin synthesis inhibitors. Administration 1 hour after the NSAID treatment gave practically a total protection of the gastric mucous membrane.

Example I.3.

The pilorus of Shay rats of 150–170 g weight was tied in ether narcosis /Gastroenterology 5,43,1945/. The test substances were added on the course of operation intraduodenally. Immediately after operation each rat obtained 0.50 ml s.c. of a physiological salt solution for hydration. After 4 hours the rats were over-anesthesized, the stomach liquid was collected, centrifugated and the volume determined. Acidity of the secretion was determined with 0.1N aqueous sodium hydroxide in the presence of a Töbfler reagent.

Measurement of stimulated secretion of gastric acid was also carried out according to the above method. Immediately after ligation of the pilorus increase of secretion was induced by s.c. administration of 10 mg/kg of histamine,. The results are shown in Table III.

TABLE III

| Substance No. | dose i.d | volume ml | μEqu/4$^h$ | μEqu/ml |
|---|---|---|---|---|
| control | | 5.26 ± 0.82 | 561.0 ± 0.87 | 107 ± 10 |
| 1 | 5 | 1.4 ± 1.24* | 147.0 ± 0.19* | 105 ± 5 |
| | 10 | 0.58 ± 0.1** | 42.0 ± 0.3** | 61 ± 5*a |

*p < 0.05
**p < 0.01
*a: it was not possible to titrate part of the secretion because of the small volume, this is why there is a difference between the μEqu/4$^h$ and the μEqu/ml values.

Influencing histamine stimulated hydrochlorid acid secretion is shown in Table IV:

TABLE IV

| substance N°. | dose mg/kg | volume/4$^h$ ml | μEqu/4$^h$ | μEqu/ml |
|---|---|---|---|---|
| basal secretion | | 4.5 ± 0.6 | 575 ± 60 | 128 ± 11 |
| histamine | 10(s.c.) | 6.3 ± 0.7 | 1477 ± 80 | 237 ± 18 |
| histamine + 1 | 10(s.c.) 5(i.d.) | 1.7 ± 0.2* | 180 ± 12** | 105 ± 10* |
| | 10(i.d.) | 0.9 ± 15** | 111 ± 9** | 123 ± 8* |

*p < 0.05
**p < 0.01

Table III. and IV. demonstrate that both the basic gastric acid secretion and the acid secretion stimulated with histamine were inhibited by the test samples.

Example I.4.

Female rats of 120–130 g weight, subjected to starvation for 24 hours were treated perorally with different doses of the test substances and after 30 minutes with hydrochloric acid in ethanol (1 ml of concentrated hydrochloric acid in 50 ml of absolute ethanol). The volume of treatment was 0.5 ml/100 g. After 1 hour the animals were over-anesthesized, the average length of haemorrhages of the gastric glandular parts were measured with mm accuracy. The average degree of haemorrhages of the treated groups was compared to the control groups treated with the vehicle only. Number of animals was 6–18 in each group. The results are shown in Table V.

TABLE V

| Substance | dose mg/kg | number of animals control | number of animals treated | average length of haemmorrhages control | average length of haemmorrhages treated | * in % |
|---|---|---|---|---|---|---|
| 1 | 2.3 | 12 | 12 | 95.7 ± 9.4 | 91.0 ± 9.4 | -4 |
| | 5.0 | 18 | 18 | 92.9 ± 6.3 | 39.7 ± 8.1 | -57 |
| | 10.0 | 18 | 18 | 61.3 ± 9.8 | 14.2 ± 7.4 | -77 |
| 6 | 20.0 | 6 | 6 | 61.3 ± 9.8 | 48.0 ± 10.3 | -22 |
| 11 | 20.0 | 12 | 12 | 80.4 ± 8.2 | 51.8 ± 10.0 | -36 |
| cimetidine | 100 | | | | | |
| cimetidine | 300 | 16 | 16 | 74.8 ± 6.4 | 64.2 ± 12.3 | -24 |

* = ±SE change

It is shown above that the test samples protected the gastric mucous membran in a dose-dependent manner against lesions induced with hydrochloric acid and ethanol. Cimetidin was practically inactive at 100 mg/kg doses.

Example I.5.

The method of Szabo & et. al (Gastroenterology, 88, 228, 1985) was used for evaluation of alcohol induced increase of gastric glandular capillary permeability on rats. 15 minutes after administration of the test samples a 0.5% solution of methylene blue in water was injected i.v. After 13 minutes 1 ml of 100% ethanol was added perorally and after further 2 minutes the stomachs were removed and their weights measured. As a consequence of capillary lesions the methylene blue leaved the vascular bed, resulting in an increased blue coloration of the stomach. In order to extract the colour the glandular part was extracted for 24 hours in a solution of 1% sumarin in methanol and intensity of the colour was determined by way of photometry at 615 nm wave length after centrifugating the solution obtained. The results are shown in Table VI.

TABLE VI

| substance | dose mg/kg | stomach (g) | Evans-blue μg/g |
|---|---|---|---|
| 100% ethanol | | 1.1 ± 0.15 | 9.45 ± 0.94 |
| 100% ethanol + 1 | 20 | 0.93 ± 0.1 | 4.4 ± 0.23* |
| | 10 | 0.91 ± 0.1 | 4.55 ± 0.3* |

* = p < 0.05

The results show that alcohol-induced lesions are reduced by administration of substance 1.

Example I.6.

To investigate inhibition of stress ulcer caused by immersion Wistar rats of both sexes of 180–200 g weight were placed into a water bath of 20±1°C. 30 minutes after peroral treatment with the test substance, vertically to the level of the xiphoid process. After seven hours the glandular lesions appearing in the stomach were evaluated according to the score described in Example I.1. The results are shown in Table VII. It is evident that 50 mg/kg doses of substance 1. significally inhibit hyperemia and erosion. Cimetidin caused no significant inhibition.

TABLE VII

| Substance N° | dose mg/kg p.o. | n | hyperemia ulcer-index mm | hyperemia inhibition % | erosion ulcus-index mm | erosion inhibition % |
|---|---|---|---|---|---|---|
| control | | 10 | 80.1 ± 7.3 | | 42.4 ± 8.3 | |
| 1 | 10 | 7 | 64.3 ± 8.6 | 29 | 33.6 ± 10.2 | 21 |
| | 25 | 10 | 35.8 ± 9.4 | 55** | 12.1 ± 3.6 | 71** |
| | 50 | 7 | 11.4 ± 2.8 | 85** | 5.7 ± 1.5 | 87** |
| control | | | 73.4 ± 6.9 | | 36.9 ± 7.2 | |
| cimetidine | 100 | 7 | 58.1 ± 10.4 | 21 | 24.4 ± 10.0 | 34 |
| | 200 | 7 | 48.2 ± 14.6 | 39 | 18.2 ± 11.2 | 50 |

** = p < 0.01

Example I.7.

To investigate influence of gastric blood-supply the tests were carried out according to the method of Sapirstain using Rb$^{86}$ isotopes (Circ.Res.4, 689, 1956; Am. J. Physiol. 193. 161,1958). The test substances were administered perorally 2 hours before the experiment started and the degree of blood flow was determined in ml/min/g values. In the experiments the stomachs of Wistar female rats were divided into three segments i.e. pre-stomach, corpus and antrum. The results are shown in Table VIII.

Table VIII illustrates that the test samples increase blood-flow in the gastric body and antrum while there was no change in the pregastric region.

TABLE VIII

| substance | dose | | blood flow ml/min/g ± SE | | |
|---|---|---|---|---|---|
| No. | mg/kg | n | pre-stomach | corpus | anthrum |
| control | | 11 | 0.23 ± 0.03 | 0.51 ± 0.03 | 0.71 ± 0.07 |
| 1 | 100 | 11 | 0.19 ± 0.01 | 0.70 ± 0.09* | 1.01 ± 0.07 |

* = $p < 0.02$

Example I.8.

Female OFA rats of 130–160 g weight, starved for 24 hours, were treated at the same time perorally with 40 mg/kg doses of the substances to be tested and with 5 mg/kg s.c. doses of reserpine. After 18 hours the animals were over-anesthesized and the removed stomachs were investigated under stereomicroscope using a 8-fold enlargement. The number of ulcers was counted and their size was evaluated using 0-0.5-1-2-4-8-16-32 scores. The number of animals was 5 for each dose. Results (%change compared with control) are shown in Table IX.

TABLE IX

| substance N° | mg/kg | number of ulcers | severity of ulcers | ulcers per treated |
|---|---|---|---|---|
| 1 | 40 | +4 | +9 | 5/5 |
| 6 | 40 | +17 | −5 | 5/5 |
| 11 | 40 | +67 | +37 | 5/5 |

Table IX. demonstrates that the number and severity of ulcers is not decreased by the test samples, as compared to the control, thus they are ineffective against ulcers induced by reserpine. This indicates that their ulcer inhibiting activity is not a result of an influence on the cholinergic system.

Example I.9.

To determine acute toxicity the test substances were administered in increasing doses to CFLP male mice (18–20 g) and to male Wistar rats (150–160 g). The $LD_{50}$ values were calculated after 14 days of observation according to Litchfield and Wilcoxon. The results are shown in Table X:

TABLE X

| substance | species | $LD_{50}$ mg/kg per os |
|---|---|---|
| 1 | mice | 840 (720–890) |
| | rats | 560 (480–610) |

II. Examples for compositions

Example II.1. Composition for intravenous injection
Components:
  Active ingredient of general formula (I) 0.03 g (e.g. Substance N°1 to 10)
  Propylene glycol 20.0 g
  Polyethylene glycol 400 20.2 g
  Tween 80 1.2 g
  0.9% Aqueous solution of sodium chloride ad 1000.0 ml.
Method:
The active ingredient is dissolved in the mixture of propylene glycol, polyethylene glycol and Tween 80 whereupon the amount of an aqueous solution containing 0.9% of sodium chloride needed to complete the volume to 1000 ml is added. The solution is filtered on a membrane filter of 0.2µpore size and filled into ampoules under sterile conditions.

Example II.2. Capsules
Components:
  Active ingredient 250 mg
  Magnesium stearate 20 mg
The above components are admixed dry and filled into capsules of 500 µl volume.

Example II.3. Tablets
Components:
Active ingredient 100 mg
Cellulose 10 mg
Lactose 20 mg
Magnesium stearate 2 mg
Polyvinyl-pyrrolidone /PVP/ 3 mg
Granules containing the active ingredient are prepared by kneading the active ingredient with cellulose, lactose and a solution of PVP in ethanol. The granules obtained are dried, mixed with magnesium stearate and the tablet-material is pressed to form tablets in the usual manner.

III. Chemical Examples

Example III.1.

3.27 g of 4-chloro-quinoline, 1.38 g of 1H-1,2,4-triazole and 0.21 g of 1H-1,2,4-triazole hydrochloride are mixed in 10 ml of dimethyl-formamide for 1 hour at 80° C. The reaction mixture is added to 50 ml of water, neutralized with cc. aqueous ammonia, the precipitate is filtered, washed with water and recrystallized from 15 ml of ethanol. 2.47 g /63%/ of 4-(1H-1,2,4-triazole-1-yl)-quinoline (Substance 1) are obtained. M.p.:147°–149° C.

Example III.2.

1.98 g of 4,7-dichloro-quinoline and 1.38 g of 1H-1,2,4-triazole are reacted in 10 ml of dimethyl formamide and worked up as described in Example 1. 2.6 g of 4-(1H-1,2,4-triazole-1-yl)-7-chloro-quinoline (Substance 2) are obtained.

M.p.:169°–170° C.

Example III.3.

1.64 g of 2-chloro-quinoline and 1.1 g of the sodium salt of 1H-1,2,4-triazole are reacted in 10 ml of dimethyl formamide for 20 hours at 100° C. and worked up as in Example 1 to give 1.43 g of 2-(1H-1,2,4-triazole-1-yl)-quinoline /yield 53%/

M.p.:107–109° C. (Substance 5).

Using similar methods along with the suitable starting materials the following products are obtained:

| Ex. | N° | Product | Yield % | M.p. °C. |
|---|---|---|---|---|
| III.4. | 3. | 4-(1H-1,2,4-triazole-1-yl)-7-methyl-quinoline | 69 | 179–180 |
| III.5. | 4. | 2-methyl-4-(1H-1,2,4-triazole-1-yl)-quinoline | 62 | 95–96 |
| III.6. | 6. | 2-(1H-1,2,4-triazole-1-yl)-3-methyl-quinoline | 69 | 87–89 |
| III.7. | 7. | 2-(1H-1,2,4-triazole-1-yl)-3-methyl-7-bromo-quinoline | 92 | 122–123 |
| III.8. | 8. | 2-(1H-1,2,4-triazole-1-yl)-3-methyl-7-ethyl-quinoline | 64 | 72–73 |
| III.9. | 9. | 2-methyl-4-(1H-1,2,4-triazole-3-yl-thio)-quinoline | 89 | 180–182 |
| III.10 | 10. | 2,5,7-trimethyl-4-(5-ethyl-1H-1,2,4-triazole-3-yl-thio)-quinoline | 69 | 198–201 |
| III.11 | 11. | 2-(1H-1,2,4-triazole-3-yl-thio)-3-methyl-quinoline | 83 | 150–151 |
| III.12 | 12. | 2-(5-ethyl-1H-1,2,4-triazole-3-yl-thio)-3-methyl-quinoline | 85 | 487–189 |

Example III.13.

3.21 g of 4-(1H-2,3,4-triazole-1-yl)-quinoline-hydrochloride are obtained (Substance N°1.HCl) from the crude product of Example 1. with HCl in ethanol. Yield: 69%. M.p.: 238°–240° C.

We claim:

1. Method for the treatment or prevention of lesions of gastrointestinal mucous membranes and for inhibiting secretion or for cytoprotective activities characterized by administering to a patient in need of such treatment a quinoline derivative of general formula (II)

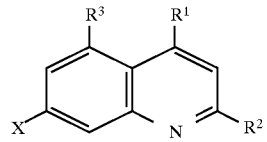

wherein $R_1$ is selected from the group consisting of a 1-triazolyl-group or a 3-triazolyl-thio or a 5-/$C_{1-4}$-alkyl/-3-triazolyl-thio group, $R_2$ is selected from the group consisting of a hydrogen atom or a $C_{1-4}$ alkyl group, $R_3$ is selected from the group consisting of a hydrogen atom or a $C_{1-4}$ alkyl group, and X is selected from the group consisting of a hydrogen or halogen atom or a $C_{1-4}$ alkyl group;

or its salts in a biologically effective quantity.

2. Method for the treatment or prevention of lesions of gastrointestinal mucous membranes and for inhibiting secretion or for cytoprotective activities characterized by administering to a patient in need of such treatment a quinoline derivative of general formula (III)

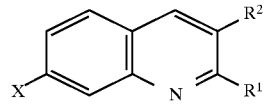

wherein $R_1$ is selected from the group consisting of a 1-triazolyl-group or a 3-triazolyl-thio or a 5-/$C_{1-4}$-alkyl/-3-triazolyl-thio group, $R_2$ is selected from the group consisting of a hydrogen atom or a $C_{1-4}$ alkyl group, and X is selected from the group consisting of a hydrogen or halogen atom or a $C_{1-4}$ alkyl group;

or its salts in a biologically effective quantity.

3. Method for the treatment or prevention of lesions of gastrointestinal mucous membranes, for inhibiting secretion or for cytoprotection especially for the treatment or prevention of ulcer, characterized by administering to a patient in need of such treatment a quinoline derivative of general formula (I)

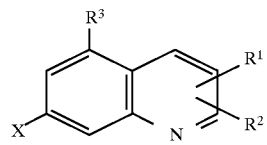

wherein $R_1$ is selected from the group consisting of a 1-triazolyl-group in position 2 or 4 or a 3-triazolyl-thio or a 5-/$C_{1-4}$-alkyl/-3-triazolyl-thio group, $R_2$ is selected from the group consisting of a hydrogen atom in position 3 or position 2 , or a $C_{1-4}$ alkyl group, $R_3$ is selected from the group consisting of a hydrogen atom or a $C_{1-4}$ alkyl group, and X is selected from the group consisting of a hydrogen or halogen atom or a $C_{1-4}$ alkyl group;

or its salts.

4. The method of claim 3, wherein said quinoline derivative of general formula (I) is 4-(1H-1, 2, 4-triazole-1-yl)-quinoline and its salts.

5. The method of claim 3, further comprising administering an active ingredient having anti-inflammatory activity before, together or after said quinoline derivative of general formula (I).

6. The method of claim 5, wherein said active ingredient having anti-inflammatory activity is a nonsteroidal anti-inflammatory drug.

7. The method of claim 6, wherein said nonsteroidal anti-inflammatory drug is selected from the group consisting of indomethacin, piroxicam, naproxen, salicilates, ibuprofen and diclofenac.

8. The method of claim 3, wherein said step of administering to the patient is selected from the group consisting of oral, parenteral or rectal administration.

9. The method of claim 8 wherein said step of administering comprises administration of a daily dose of 5 to 30 mg active ingredient per kg body weight of said patient.

10. The method of claim 1, further comprising administering an active ingredient having anti-inflammatory activity before, together or after said quinoline derivative of general formula (II).

11. The method of claim 10, wherein said active ingredient having anti-inflammatory activity is a nonsteroidal anti-inflammatory drug.

12. The method of claim 11, wherein said nonsteroidal anti-inflammatory drug is selected from the group consisting of indomethacin, piroxicam, naproxen, salicilates, ibuprofen and diclofenac.

13. The method of claim 1, wherein said step of administering to the patient is selected from the group consisting of oral, parenteral or rectal administration.

14. The method of claim 1 wherein said step of administering comprises administration of a daily dose of 5 to 30 mg active ingredient per kg body weight of said patient.

15. The method of claim 2, further comprising administering an active ingredient having anti-inflammatory activity before, together or after said quinoline derivative of general formula (II).

16. The method of claim 15, wherein said active ingredient having anti-inflammatory activity is a nonsteroidal anti-inflammatory drug.

17. The method of claim 16, wherein said nonsteroidal anti-inflammatory drug is selected from the group consisting of indomethacin, piroxicam, naproxen, salicilates, ibuprofen and diclofenac.

18. The method of claim 2, wherein said step of administering to the patient is selected from the group consisting of oral, parenteral or rectal administration.

19. The method of claim 2 wherein said step of administering comprises administration of a daily dose of 5 to 30 mg active ingredient per kg body weight of said patient.

* * * * *